(12) United States Patent  
Fuchiwaki et al.

(10) Patent No.: US 12,400,740 B2  
(45) Date of Patent: Aug. 26, 2025

(54) CHEMICAL STRUCTURE GENERATING DEVICE, CHEMICAL STRUCTURE GENERATING PROGRAM, AND CHEMICAL STRUCTURE GENERATING METHOD

(71) Applicant: JSR CORPORATION, Tokyo (JP)

(72) Inventors: Junta Fuchiwaki, Tokyo (JP); Yoshio Takimoto, Tokyo (JP)

(73) Assignee: JSR Corporation, Tokyo (JP)

( * ) Notice: Subject to any disclaimer, the term of this patent is extended or adjusted under 35 U.S.C. 154(b) by 823 days.

(21) Appl. No.: 17/671,745

(22) Filed: Feb. 15, 2022

(65) Prior Publication Data

US 2022/0172803 A1 Jun. 2, 2022

Related U.S. Application Data

(63) Continuation of application No. PCT/JP2020/031178, filed on Aug. 18, 2020.

(30) Foreign Application Priority Data

Aug. 19, 2019 (JP) .................................. 2019-149873

(51) Int. Cl.
*G16C 20/10* (2019.01)
*G16C 20/70* (2019.01)

(52) U.S. Cl.
CPC ............. *G16C 20/10* (2019.02); *G16C 20/70* (2019.02)

(58) Field of Classification Search
CPC .................................. G16C 20/10; G16C 20/70
USPC ........................................................... 703/2
See application file for complete search history.

(56) References Cited

U.S. PATENT DOCUMENTS

| 2003/0203400 | A1 | 10/2003 | Strehlau et al. |
| 2015/0310162 | A1 | 10/2015 | Okuno et al. |
| 2018/0096100 | A1 | 4/2018 | Alzate et al. |

FOREIGN PATENT DOCUMENTS

| CA | 3235430 A1 * | 4/2023 | ............. G06N 3/045 |
| JP | 2001058962 | 3/2001 | |
| WO | 95/01606 | 1/1995 | |
| WO | 97/36252 | 10/1997 | |
| WO | 2014/034577 | 3/2014 | |

OTHER PUBLICATIONS

First office Action received for Chinese Patent Application No. 202080058612.X issued on May 28, 2024, 13 pages with English translation.

(Continued)

*Primary Examiner* — Justin C Mikowski
(74) *Attorney, Agent, or Firm* — Grüneberg and Myers PLLC

(57) ABSTRACT

A chemical structure generating device according to the present invention includes a generator and a controller. The generator produces a product list including one or more compounds, based on a reactant list including one or more compounds and a chemical reaction list. The controller applies the product list as a new reactant list to the generator, updates a database having at least one list of the reactant list and the product list, and allows the generator to produce a new product list based on the new reactant list and the chemical reaction list.

14 Claims, 6 Drawing Sheets

(56) References Cited

OTHER PUBLICATIONS

Notice of Reasons for Refusal received for Japanese Patent Application No. 2021-540953 mailed on Jul. 3, 2024, 6 pages with English translation.
International Search Report issued Nov. 17, 2020 in PCT/JP2020/031178, with English translation, 5 pages.
Written Opinion issued Nov. 17, 2020 in PCT/JP2020/031178, with English translation, 8 pages.
Yoshikawa, Shunsuke, "Research on construction of virtual compound library by graph structure transformation with directionality" [unofficial translation]; "1. 2 Purpose of research" on p. 1, "3.2 Overview of library construction" on p. 3; IPSJ Technical Report Bio information science (BIO) [online], 2015-BI0-41, No. 12, pp. 1-6, Mar. 2015.
Japanese Notice of Reasons for Refusal dated Feb. 20, 2024, in Japanese patent application No. 2021-540953, with English translation, 8 pages.
Notice of Reasons for Refusal in Japanese Application No. 2024-068187 mailed on Jun. 25, 2025, 6 pages with English translation.

* cited by examiner

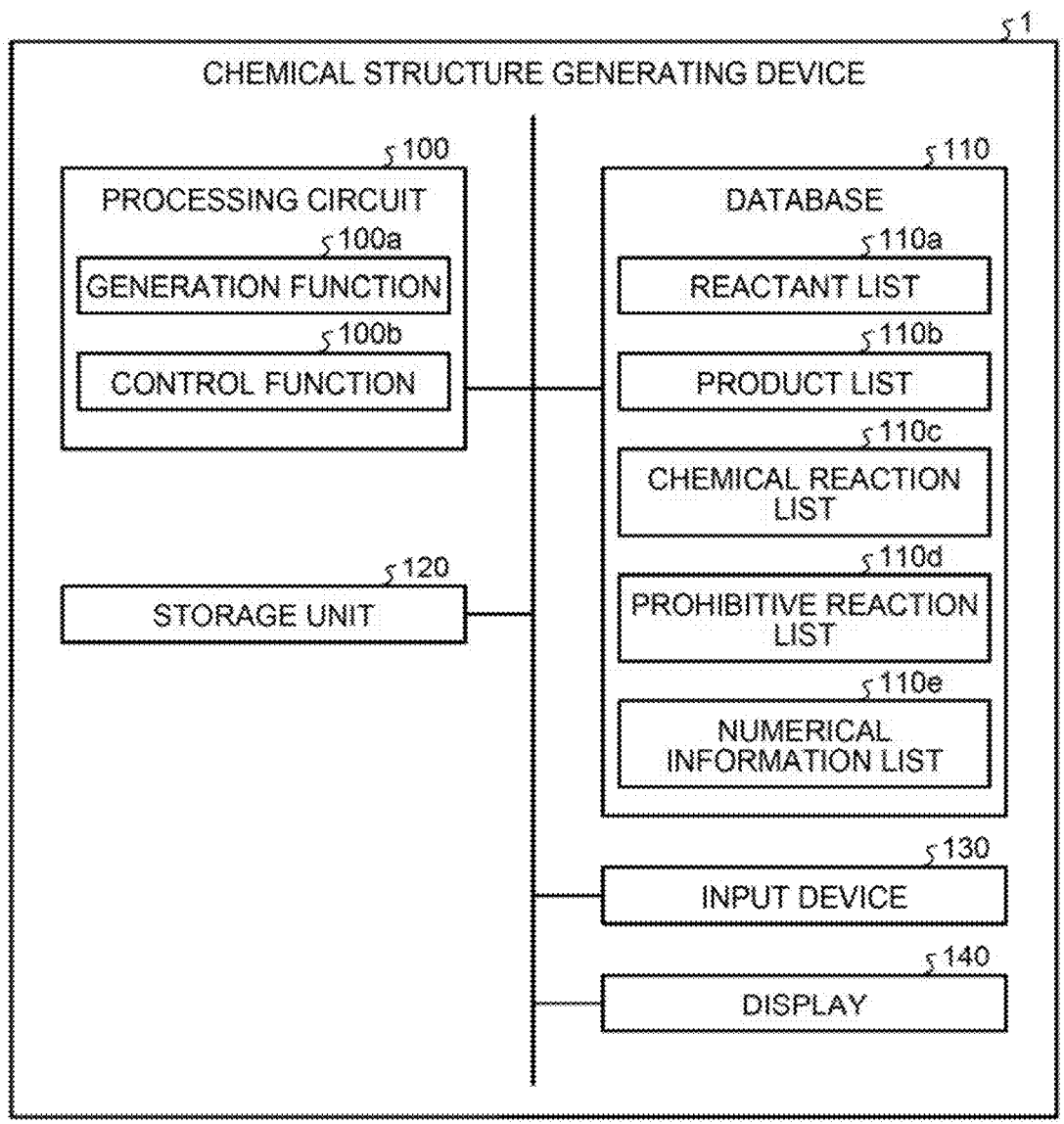

| MOLECULAR STRUCTURE 1 | MOLECULAR STRUCTURE 2 | GENERATED STRUCTURE | Rule |
|---|---|---|---|
| $X_1$-COOH | $X_2$-H | $X_1$-CO-$X_2$ | Allow |
| $X_1$-COOH | $X_2$-CO-$CH_2$-CO-$X_3$ | $X_2$-CO-$CHX_1$-CO-$X_3$ | Deny |

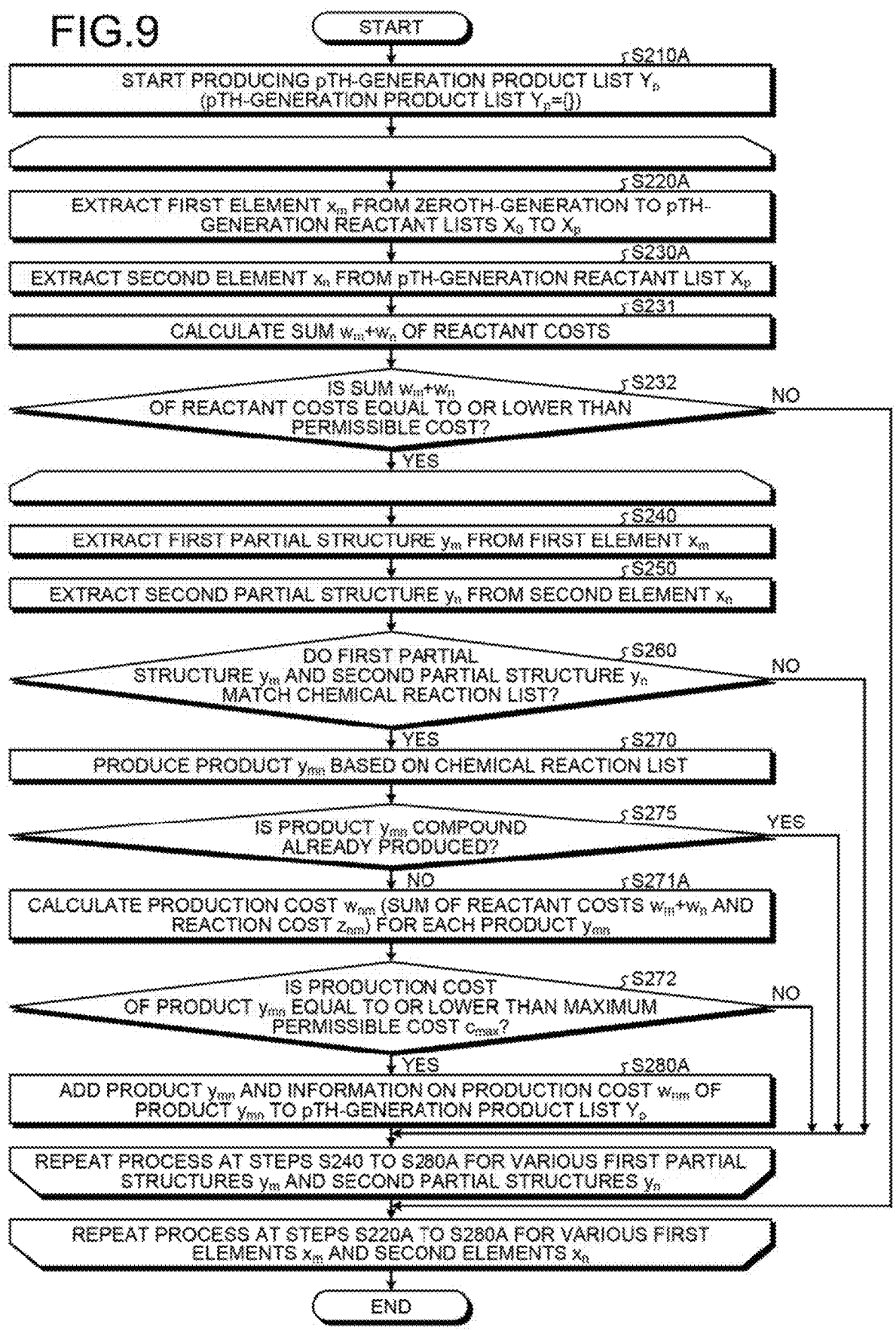

CHEMICAL STRUCTURE GENERATING DEVICE, CHEMICAL STRUCTURE GENERATING PROGRAM, AND CHEMICAL STRUCTURE GENERATING METHOD

CROSS-REFERENCE TO RELATED APPLICATION

This application is a continuation of PCT International Application No. PCT/JP2020/031178 filed on Aug. 18, 2020 which claims the benefit of priority from Japanese Patent Application No. 2019-149873 filed on Aug. 19, 2019, the entire contents of which are incorporated herein by reference.

BACKGROUND OF THE INVENTION

1. Field of the Invention

The present invention relates to a chemical structure generating device, a chemical structure generating program, and a chemical structure generating method.

2. Description of the Related Art

There is interest in methods to design molecules having useful properties by machine learning using computer simulations. As an example, first, in a learning phase, a trained model is produced by machine learning such as deep learning using a training dataset, and then in an execution phase, for example, prediction of physical property values or search for molecules having desired physical properties is performed using the trained model produced in the learning phase.

Since performing machine learning such as deep learning requires a large volume of training data, how high-quality training data is efficiently produced is important. In view of this, a chemical structure generating device that automatically generates molecular structures appropriate for use as training data in machine learning is important.

Here, as the number of atoms increases, the number of possible molecular structures for the number of atoms exponentially increases to cause a combinatorial explosion. It is therefore actually impossible to exhaustively generate molecular structure candidates. In addition, the ratio of the number of usable molecules, that is, molecules actually stably existing and commercially usable to the number of possible molecular structures rapidly decreases as the number of atoms increases. In performing machine learning, it is extremely inefficient in terms of time and economy to use training data including many molecular structures commercially unusable. There is therefore a demand for a chemical structure generating device capable of efficiently generating only molecules commercially usable and valuable. Conventional technologies are described in WO 9501606, United States Patent Application No. 2018/096100, Japanese Patent Application Laid-open No. 2001-058962, and WO 9736252, for example.

SUMMARY OF THE INVENTION

It is an object of the present invention to at least partially solve the problems in the conventional technology.

It is an object of the present invention to efficiently generate molecular structures suitable for use as training data for machine learning.

In order to solve the problems and to achieve the object, a chemical structure generating device of the present invention comprises a generator and a controller. The generator produces a product list including one or more compounds, based on a reactant list including one or more compounds and a chemical reaction list. The controller applies the product list as a new reactant list to the generator, update a database having at least one list of the reactant list and the product list, and allow the generator to produce a new product list based on the new reactant list and the chemical reaction list.

Further, a chemical structure generating program of the present invention causes a computer to perform:
a process of producing a product list including one or more compounds, based on a reactant list including one or more compounds and a chemical reaction list;
a process of applying the product list as a new reactant list;
a process of updating a database having at least one list of the reactant list and the product list; and
a process of producing a new product list based on the new reactant list and the chemical reaction list.

Further, a chemical structure generating method of the present invention is a method performed by a chemical structure generating device, the chemical structure generating method comprising:
producing a product list including one or more compounds, based on a reactant list including one or more compounds and a chemical reaction list;
applying the product list as a new reactant list;
updating a database having at least one list of the reactant list and the product list; and
producing a new product list based on the new reactant list and the chemical reaction list.

According to the present invention, it is possible to efficiently generate molecular structures suitable for use as training data for machine learning.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 1 is a diagram illustrating an overview of a chemical structure generating device according to embodiments of the present invention;

FIG. 2 is a diagram illustrating an example of a chemical reaction list in the chemical structure generating device according to a first embodiment;

FIG. 9 is a flowchart illustrating the detail of the process at step S200A in FIG. 8.

DETAILED DESCRIPTION OF THE PREFERRED EMBODIMENTS

Figures 3, 4:
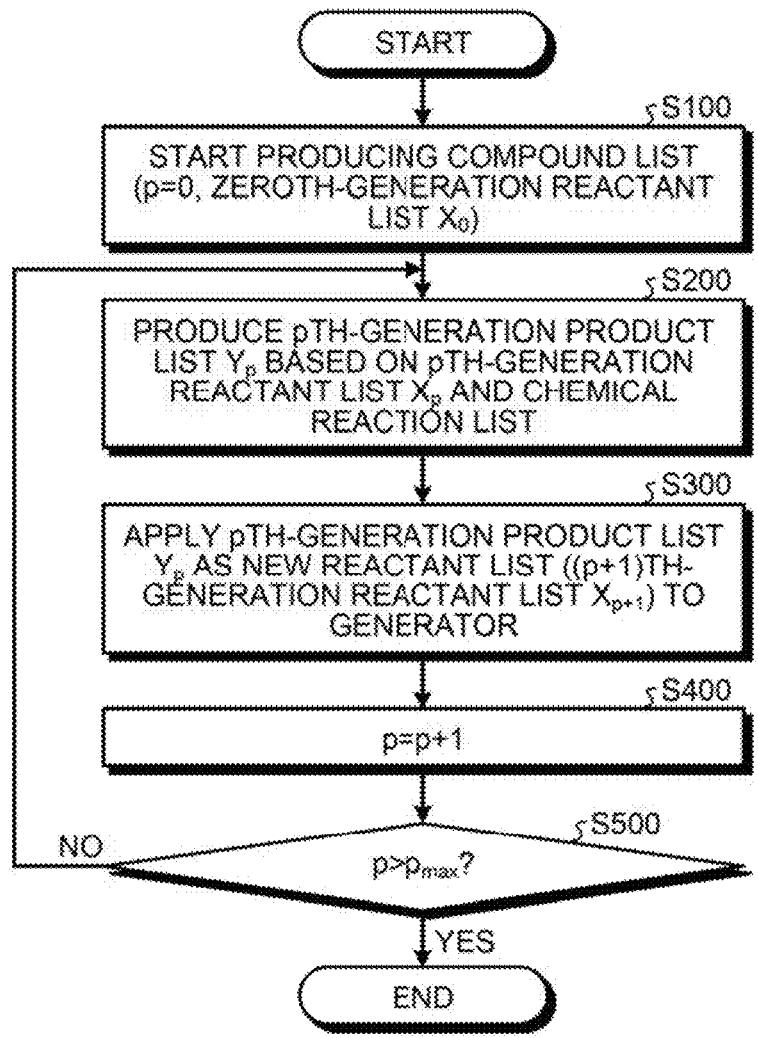
FIG. 3 is a diagram illustrating an example of a prohibitive reaction list in the chemical structure generating device according to the first embodiment.
FIG. 4 is a flowchart illustrating a process performed by the chemical structure generating device according to the first embodiment.

A chemical structure generating device according to embodiments of the present invention will be described below with reference to the accompanying drawings.

First Embodiment

FIG. 1 is a diagram illustrating an overview of a chemical structure generating device 1 according to embodiments of the present invention. The chemical structure generating device 1 includes a processing circuit 100, a storage unit 120, a database 110, an input device 130, and a display 140. The processing circuit 100 includes a generation function 100a and a control function 100b. The database 110 includes a reactant list 110a that is a list of reactants and the like of chemical reactions, a product list 110b that is a list of products and the like of chemical reactions, a chemical reaction list 110c, a prohibitive reaction list 110d, and a numerical information list 110e. The chemical structure generating device 1 is a device for generating chemical structures serving as a basis for training data for use in machine learning, in the form of the reactant list 110a or the product list 110b.

The processing circuit 100 is a processor (for example, a central processing unit (CPU), a graphical processing unit (GPU), an application specific integrated circuit (ASIC), or a programmable logic device (PLD)) that reads and executes a computer program from the storage unit 120 to implement functions such as the generation function 100a and the control function 100b. That is, the processing functions including the generation function 100a and the control function 100b are stored in the storage unit 120 in the form of a computer program executable by the processor. The processing circuit 100 in a state in which the computer program has been read has functions such as the generation function 100a and the control function 100b. In other words, the generation function 100a and the control function 100b are an example of the generator and the controller, respectively. The detail of the process in each function of the processing circuit 100 will be described later.

The database 110 is a variety of databases referred to by the processing circuit 100 in a process of generating new compounds by the chemical structure generating device 1 and is configured with, for example, the reactant list 110a, the product list 110b, the chemical reaction list 110c, the prohibitive reaction list 110d, and the numerical information list 110e. These databases are stored in the storage unit 120 if necessary.

The chemical reaction list 110c, the prohibitive reaction list 110d, and the numerical information list 110e are data used by the processing circuit 100 to perform the process of generating chemical structures. On the other hand, the reactant list 110a or the product list 110b is data serving as a basis for training data used in machine learning at a subsequent stage, and producing these lists is one of the objects of the process performed by the chemical structure generating device 1.

The reactant list 110a is a list of reactants serving as a basis for chemical reactions and includes compounds representing the reactants. More precisely, the reactant list 110a includes one or more elements, and each of the elements is a single element, a compound, an element representing an operation of not selecting a reactant, or an element representing an intramolecular reaction. Here, the chemical structure generating device 1 according to the embodiments successively updates the reactant list, starting from an initial compound. The reactant list 110a therefore includes an initial-state (zeroth-generation (p=0)) reactant list $X_0$, a first-generation reactant list $X_1$, a second-generation reactant list $X_2$, ..., and a pth-generation reactant list $X_p$. Here, a (k+1)th generation reactant list $X_{k+1}$ may completely include a kth-generation reactant list $X_k$, or the (k+1)th generation reactant list $X_{k+1}$ need not completely include the kth-generation reactant list $X_k$.

The reactant list $X_k$ of each generation may include special compounds $x_{null}$ and $x_{intra}$ indicating a special operation as optional constituent elements, in addition to compounds $x_{k1}$ ... $x_{kn}$ representing reactants. These special compounds will be described later. When these special compounds are not included as elements, the elements of the kth-generation reactant list $X_k$ are compounds $x_{k1}, x_{k2}$ ..., $x_{kn}$ representing kth-generation reactants. Conversely, when these special compounds are included as elements, the elements of the kth-generation reactant list $X_k$ are, for example, $x_{k1}, x_{k2}$ ..., $x_{kn}, x_{null}, x_{intra}$.

The product list 110b is a product list of chemical reactions and includes compounds representing products. More precisely, the product list 110b includes one or more elements, and each of the elements is a single element, a compound, an element representing an operation of not selecting a reactant, or an element representing an intramolecular reaction. Here, the product list 110b includes a zeroth-generation (p=0) product list $Y_0$, a first-generation product list $Y_1$, a second-generation product list $Y_2$, ..., and a pth-generation product list $Y_p$, in the same manner as the reactant list 110a.

In some embodiments, the elements of the (k+1)th-generation reactant list $X_{k+1}$ are equal to the elements of the kth-generation product list $Y_k$.

The chemical reaction list 110c is a possible chemical reaction list and is a list in which a list of partial structures of a reactant is associated with a list of partial structures of a product produced by a chemical reaction using the reactant. The chemical reaction list 110c also includes information on the cost of the chemical reaction, if necessary.

FIG. 2 illustrates an example of the chemical reaction list 110c with two or one reactant and one product corresponding thereto.

The first row of FIG. 2 provides a case where a structure "$X_1$—CO—$X_2$" is generated from a partial structure "$X_1$—COOH" and a partial structure "$X_2$—H". In such a case, a list {{"$X_1$—CO—$X_2$"}, {"$X_1$—COOH", "$X_2$—H"}} in which a partial structure list of reactants {"$X_1$—COOH", "$X_2$—H"} is associated with a partial structure list of a product {"$X_1$—CO—$X_2$"} produced by the chemical reaction is an example of the chemical reaction list 110c.

The second row of FIG. 2 provides a case where a structure "$X_1$—CHOH—$X_2$" is generated from a partial structure "$X_1$—CO—$X_2$". In such a case, a list {{"$X_1$—CHOH—$X_2$"}, {"$X_1$—CO—$X_2$"}} in which a partial structure list of a reactant {"$X_1$—CO—$X_2$"} is associated with a partial structure list of a product ("$X_1$—CHOH—$X_2$") produced by the chemical reaction is an example of the chemical reaction list 110c. Assuming that $H_2$ is also a partial structure, this chemical reaction may be represented by {{"$X_1$—CHOH—$X_2$"}, {"$X_1$—CO—$X_2$", "$H_2$"}}.

The third row of FIG. 2 provides a case, for example, where a structure "$X_1$—$CHX_3$—$X_2$" is generated from a partial structure "$X_1$—CHOH—$X_2$" and a partial structure "$X_3$—H". In such a case, a list {{"$X_1$—$CHX_3$—$X_2$"}, {"$X_1$—CHOH—$X_2$", "$X_3$—H"}} in which a partial structure list of reactants {"$X_1$—CHOH—$X_2$", "$X_3$—H"} is associated with a partial structure list of a product ("$X_1$—$CHX_3$—$X_2$") produced by the chemical reaction is an example of the chemical reaction list 110c.

FIG. 2 illustrates the cases with two or one reactant and one product corresponding thereto. However, the embodiments are not limited thereto, and the number of reactants may be three or more. For example, when a structure D is generated from a partial structure A, a partial structure B, and a partial structure C, a list {{D}, {A,B,C}} in which a partial structure list of reactants {A,B,C} is associated with a partial structure list of a product {D} produced by the chemical reaction is an example of the chemical reaction list 110c.

In the cases described above, the number of products is one. However, the embodiments are not limited thereto and the number of products may be two or more. For example, as a reverse reaction of the first row of FIG. 2, a case where a structure "$X_1$—COOH" and a structure "$X_2$—H" are generated from a partial structure "$X_1$—CO—$X_2$" will be discussed. In such a case, a list {{"$X_1$—COOH", "$X_2$—H"}, {"$X_1$—CO—$X_2$"}} in which a partial structure list of a reactant {"$X_1$—CO—$X_2$"} is associated with a partial structure list of products {"$X_1$—COOH", "$X_2$—H"} produced by the chemical reaction is an example of the chemical reaction list 110c.

What is described above is represented by a formula as follows. For example, when a new structure $y_{kl}'$ is produced from a partial structure $y_k$ and a partial structure $y_l$, a list {{$y_{kl}'$}, {$y_k$, $y_l$}} is the chemical reaction list 110c. In general, when new m structures $y_{q1q2...qn;1}$, $y_{q1q2...qn;2}$, ..., $y_{q1q2...qn;m}$ are produced from n partial structures $y_{q1}$, $y_{q2}$ ... $y_{qn}$, a list {{$y_{q1q2...qn;1}$, $y_{q1q2...qn;2}$, ..., $y_{q1q2...qn;m}$}, {$y_{q1}$, $y_{q2}$ ... $y_{qn}$}} is the chemical reaction list 110c.

In some embodiments, unlike the reactant list 110a or the product list 110b, the elements of the chemical reaction list 110c are not updated for each generation, and the elements are fixed throughout generations.

The prohibitive reaction list 110d is a list of prohibited chemical reactions and is a list in which a partial structure list of reactants and a partial structure list of products produced by a chemical reaction using the reactant(s) are associated together with information that it is a prohibited chemical reaction.

For example, when a new structure $y_{kl}'$ is produced from a partial structure $y_k$ and a partial structure $y_l$, if the new structure to be produced has no commercial value and is not appropriate as a product, a list {{$y_{kl}'$}, {$y_k$, $y_l$}} is the prohibitive reaction list 110d. In general, when new m structures $y_{q1q2...qn;1}$, $y_{q1q2...qn;2}$, ..., $y_{q1q2...qn;m}$ are produced from n partial structures $q_{q1}$, $q_{q2}$ ... $q_{qn}$, if the product is not appropriate as a product for the reasons such as no commercial value of the product, a list {{$y_{q1q2...qn;1}$, $y_{q1q2...qn;2}$, ..., $q_{q1q2...qn;m}$}, {$y_{q1}$, $y_{q2}$ ... $y_{qn}$}} is the prohibitive reaction list 110d. The presence or absence of commercial value is determined depending on the fields, for example, in terms of cost, stability, toxicity, and the like.

FIG. 3 illustrates an example of the prohibitive reaction list 110d. FIG. 3 is a diagram for explaining a process related to the prohibitive reaction list 110d.

The upper section of FIG. 3 provides a case where a structure "$X_1$—CO—$X_2$" is generated from a partial structure "$X_1$—COOH" and a partial structure "$X_2$—H". Since there is no particular reason to limit generation of such a structure, generation of this structure is allowed (Allow).

On the other hand, the lower section of FIG. 3 provides a case where a structure "$X_x$—CO—$CHX_1$—CO—$X_3$" is generated from a partial structure "$X_1$—COOH" and a partial structure "$X_2$—CO—$CH_2$—CO—$X_3$". When it is determined that the produced structure is chemically unstable and has no commercial value in a certain field, for example, generation of such a structure is prohibited, and generation of this structure is denied (Deny). Specifically, a list {{"$X_2$—CO—$CHX_1$—CO—$X_3$"}, {"$X_1$—COOH", "$X_2$—CO—$CH_2$—CO—$X_3$"}} is the prohibitive reaction list 110d.

The numerical information list 110e is a numerical information list representing the cost and the like of each compound in the reactant list 110a. The numerical information list 110e will be described in detail in a second embodiment.

The storage unit 120 is a storage area such as a random access memory (RAM), a read-only memory (ROM), a flash memory, or a hard disk and stores a variety of computer programs to be executed by the processing circuit 100, the execution results of the computer programs, the database 110, and the like.

The input device 130 is a device for a user using the chemical structure generating device 1 to perform a variety of operations. The input device 130 is configured with, for example, a mouse, a keyboard, a touch panel, or a hardware keypad.

The display 140 shows a variety of information. For example, the display 140 shows a processing result of a CPU and a graphical user interface (GUI) for accepting a variety of operations from the user. The display 140 is configured with, for example, a liquid crystal display, an organic electro-luminescence (EL) display, or a cathode-ray tube display. The input device 130 and the display 140 may be integrated, for example, in a form such as a touch panel.

The embodiments are not limited to the foregoing examples. In some embodiments, the storage unit 120, the input device 130, the display 140, and the like are not essential components of the chemical structure generating device 1, that is, the compound generating device 1 need not include the storage unit 120, the input device 130, or the display 140. As another example, the storage unit 120, the input device 130, the display 140, and the like may be arranged outside the compound generating device 1, for example, through a network and may exchange data with the processing circuit 100.

The background of the embodiment will now be described.

There is interest in methods to design molecules having useful properties by machine learning using computer simulations. As an example, first, in a learning phase, a trained model is produced by machine learning such as deep learning using a training dataset, and then in an execution phase, for example, prediction of physical property values or search for molecules having desired physical properties is performed using the trained model produced in the learning phase.

Here, since performing machine learning such as deep learning requires a large volume of training data, how high-quality training data is efficiently produced is important. In view of this, a chemical structure generating device that automatically generates molecular structures appropriate for use as training data in machine learning is important.

Here, as the number of atoms increases, the number of possible molecular structures for the number of atoms exponentially increases to cause a combinatorial explosion. It is therefore actually impossible to exhaustively generate molecular structure candidates. In addition, the ratio of the number of usable molecules, that is, molecules actually stably existing and commercially usable to the number of possible molecular structures rapidly decreases as the number of atoms increases. In performing machine learning, it is extremely inefficient in terms of time and economy to use training data including many molecular structures commercially unusable. There is therefore a demand for a chemical structure generating device capable of efficiently generating only molecules commercially usable and valuable.

In view of such a background, the processing circuit 100 of the chemical structure generating device 1 according to the embodiments includes the generation function 100a and the control function 100b. The generation function 100a of the processing circuit 100 produces the product list 110b that is a list of products including one or more compounds, based on the reactant list 110a that is a list of reactants including one or more compounds and the chemical reaction list 110c that is a list of chemical reactions. The control function 100b of the processing circuit 100 applies the product list 110b as a new reactant list to a computer program related to the generation function 100a, updates the database 110 having at least one list of the reactant list 110a and the product list 110b, and causes the computer program related to the generation function 100a to produce a new product list based on the new reactant list and the chemical reaction list 110c.

With this process, the chemical structure generating device 1 according to the embodiments can efficiently generate high-quality training data appropriate as training data for machine learning and can enhance the efficiency of molecular design using a trained model produced using these training data.

The detail of this process will be described with reference to FIG. 4 to FIG. 7.

FIG. 4 is a flowchart illustrating a process performed by the chemical structure generating device according to a first embodiment.

First, the generation function 100a of the processing circuit 100 starts producing a compound list (step S100). The generation function 100a of the processing circuit 100 produces a pth-generation reactant list $X_p$ as the compound list while incrementing p, based on the zeroth-generation reactant list $X_0$, where p=0 in an initial state.

Subsequently, the generation function 100a of the processing circuit 100 produces a pth-generation product list $Y_p$ as the product list 110b, based on the pth-generation reactant list $X_p$ that is the reactant list 110a and the chemical reaction list 110c (step S200). That is, the generation function 100a of the processing circuit 100 produces the product list 110b including one or more compounds, based on a reactant list including one or more compounds in the reactant list 110a and the chemical reaction list 110c. The detail of the process at step S200 will be described later with reference to FIG. 6.

Subsequently, the control function 100b of the processing circuit 100 applies the pth-generation product list $Y_p$ as a new reactant list (the (p+1)th-generation reactant list $X_{p+1}$) to the computer program related to the generation function 100a (step S300). That is, the control function 100b of the processing circuit 100 applies the product list $Y_p$ produced at step S200 as a new reactant list $X_{p+1}$ to the computer program related to the generation function 100a.

In addition to performing such a process, the control function 100b of the processing circuit 100 updates the database 110 having at least one list of the reactant list 110a and the product list 110b. Here, updating the database 110 means an operation of changing elements of the database 110 by adding a new element to the database 110, for example, an operation of inputting some elements of the product list 110b as new elements of a new reactant list 110a to the database 110. For example, the control function 100b of the processing circuit 100 updates the reactant list 110a at step S300.

At least a part of the database 110 updated in this way is used, for example, as training data in machine learning. As an example, the processing circuit 100 has a not-illustrated training data producing function to produce training data in machine learning based on the updated reactant list 110a. As an example, the not-illustrated training data producing function of the processing circuit 100 may associate each of the elements of the updated reactant list 110a with the physical property value of the element to create supervised data in which a chemical structure is associated with the physical property value of the chemical structure, and the supervised data may be used as training data in machine learning. Machine learning is performed using such training data to produce a trained model, whereby the physical property value of an unknown chemical structure can be predicted and thus, for example, a chemical structure having a desired physical property value can be searched for. As another example, the not-illustrated training data producing function of the processing circuit 100 may create unsupervised data based on the updated reactant list 110a, and the unsupervised data may be used as training data in machine learning.

Subsequently, the control function 100b of the processing circuit 100 increments the value of p by 1 (step S400). Here, when the value of p is greater than a preset threshold $p_{max}$ (Yes at step S500), the process ends. That is, when the iterative generation number p exceeds the preset threshold $p_{max}$, the processing circuit 100 having the control function 100b determines that the termination condition of the product list creating process is satisfied and terminates the process. On the other hand, if the value of p is smaller than $p_{max}$ (No at step S500), the processing circuit 100 repeats the process from step S200 to step S400. Specifically, the control function 100b of the processing circuit 100 causes the computer program related to the generation function 100a to produce a new product list based on the new reactant list at step S300 and the chemical reaction list in the chemical reaction list 110c. The termination condition of the product list creating process is not limited to the one that the process is terminated when the iterative generation number p exceeds a certain iteration count. The processing circuit 100 may terminate the product list creating process based on another termination condition, for example, when the number of elements of the produced product list reaches a certain value.

Figure 5:
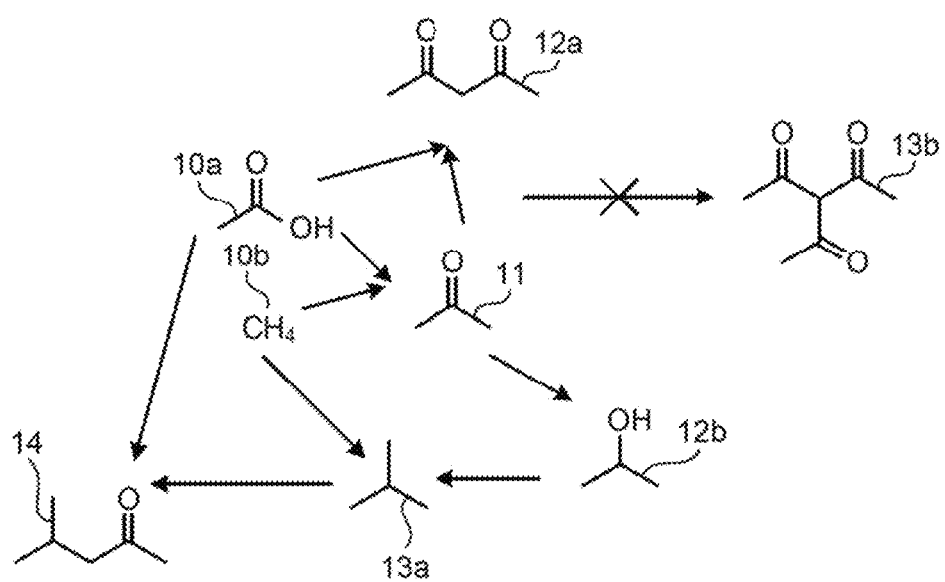
FIG. 5 is a diagram illustrating a process performed by the chemical structure generating device according to the first embodiment.

FIG. 5 illustrates an example of compounds successively produced by such a process. FIG. 5 is a diagram illustrating a process performed by the chemical structure generating device according to the first embodiment.

A compound 10a and a compound 10b denote an example of compounds included in a zeroth-generation reactant list $X_0$ in an initial state, that is, p=0. With p=0, at step S200, the generation function 100a of the processing circuit 100 produces a compound 11 as a zeroth-generation product list $Y_0$, based on the compound 10a and the compound 10b. With p=0, at step S300, the control function 100b of the processing circuit 100 applies the zeroth-generation product list $Y_0$ as a first-generation reactant list $X_1$ to the computer program related to the generation function 100a. That is, the compound 11 is included in the first-generation reactant list $X_1$. The processing circuit 100 having the control function 100b stores the product list of these produced by the generation function 100a into the storage unit 120. Subsequently, at step S400, the control function 100b of the processing circuit 100 increments the value of p by one to set p=1.

Subsequently, with p=1, at step S200, the generation function 100a of the processing circuit 100 produces a compound 12a based on the compound 10a and the compound 11 and a compound 12b based on the compound 11, as a first-generation product list $Y_1$. With p=1, at step S300, the control function 100b of the processing circuit 100 applies the first-generation product list $Y_1$ as a second-generation reactant list $X_2$ to the computer program related to the generation function 100a. That is, the compound 12a and the compound 12b are included in the second-generation reactant list $X_1$. Subsequently, at step S400, the control function 100b of the processing circuit 100 increments the value of p by one to set p=2.

Subsequently, the generation function 100a of the processing circuit 100 produces a compound 13a based on the compound 10b and the compound 12b and produces a compound 14 based on the compound 10a and the compound 13a, in the same manner. By doing so, the chemical structure generating device 1 can successively produce various compounds efficiently. In FIG. 5, the chemical reaction that produces a compound 13b from the compound 12a and the compound 11 corresponds to a chemical reaction included in the prohibitive reaction list 110d, and in such a case, the processing circuit 100 does not add the produced compound 13b to the product list.

Figure 6:
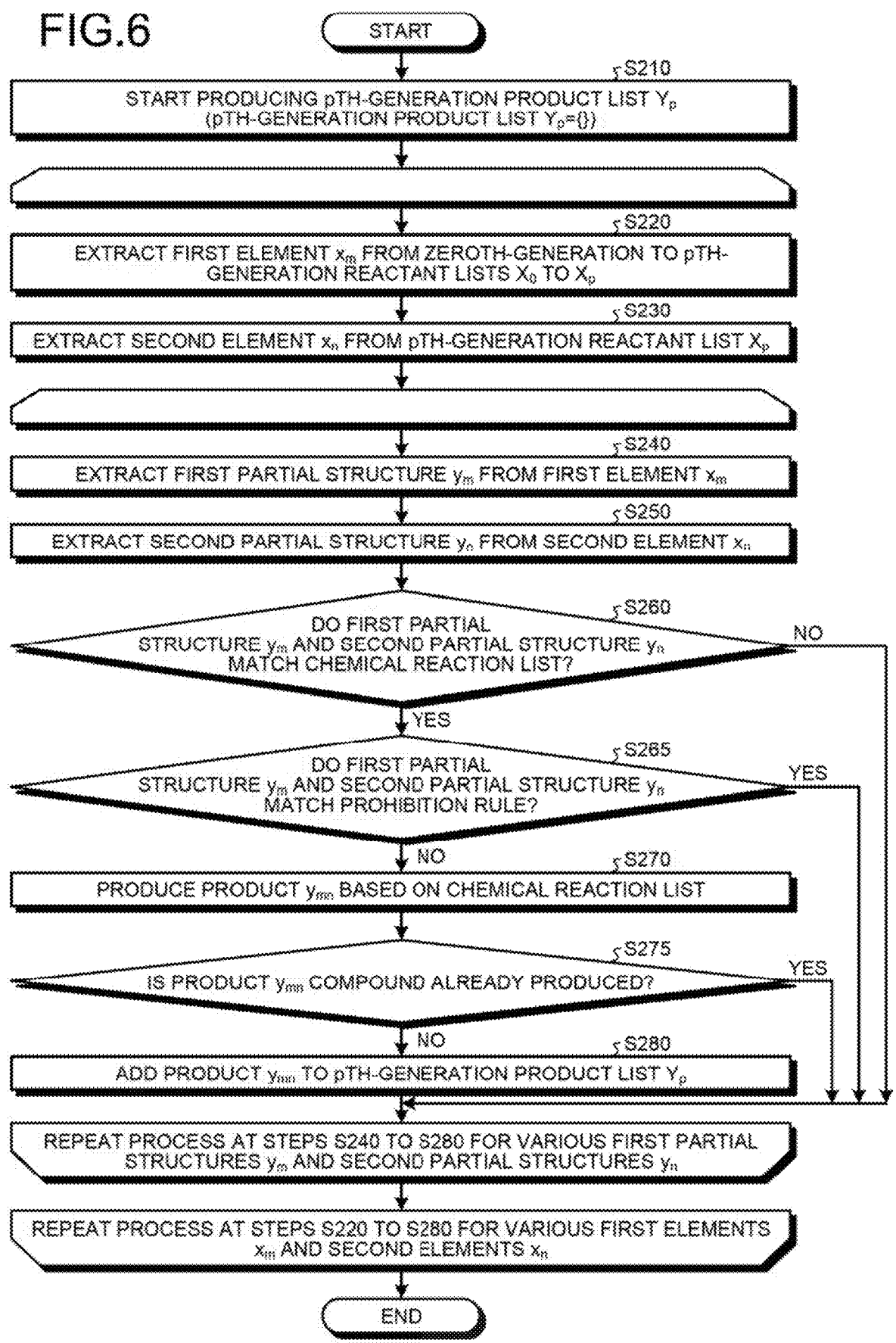
FIG. 6 is a flowchart illustrating the detail of the process at step S200 in FIG. 4.

The detail of the process at step S200 in FIG. 4 will now be described with reference to FIG. 6. That is, the flowchart in FIG. 6 is a flowchart illustrating the detail of the process at step S200 in FIG. 4.

As previously mentioned, the reactant list $X_k$ of each generation may include the special compounds $x_{null}$ and $x_{intra}$ representing special operations as optional constituent elements, in addition to the compounds $x_{k1}$ . . . $x_{kn}$ representing reactants. These special compounds will be described later. Here, a case where the reactant list $X_k$ of each generation does not include these special compounds will be described first.

In the following, in order to avoid complication of explanation, in FIG. 6, a chemical reaction used for producing a product list is a chemical reaction that produces one product from two reactants.

First of all, at step S210, the generation function 100a of the processing circuit 100 starts producing the pth-generation product list $Y_p$ in the product list 110b. Here, the generation function 100a of the processing circuit 100 starts producing the product list $Y_p$ of each pth generation, based on the zeroth-generation reactant list $X_0$, the first-generation reactant list $X_1$, the second-generation reactant list $X_2$, . . . and the pth-generation reactant list $X_p$. Immediately after the generation function 100a of the processing circuit 100 starts producing the product list $Y_p$, the product list $Y_p$ is an empty set. When the process is performed up to the $p_0$th generation, the union of the product lists $Y_0, Y_1 \ldots Y_{p0}$ produced in this way serves as data to be used as training data for machine learning. In other words, the generation function 100a of the processing circuit 100 produces data to be used as training data for machine learning, as the union of the produced product lists $Y_0, Y_1 \ldots Y_{p0}$.

First, at step 3220, the generation function 100a of the processing circuit 100 selects one element from any one reactant list among the zeroth-generation reactant list $X_0$, the first-generation reactant list $X_1$, the second-generation reactant list $X_2$, . . . and the pth-generation reactant list $X_p$, and extracts the selected element as a first element $x_m$.

For example, a case of the zeroth-generation reactant list $X_0 = \{x_{01}, x_{02}\}$ and the first-generation reactant list $X_1 = \{x_{11}, x_{12}\}$, where $x_{01}$="CH$_3$OH", $x_{02}$="CH$_4$", $x_{11}$="CH$_3$COOH", $x_{12}$="C$_2$H$_5$COOH", p=1, will be discussed. In this case, for example, at step S220, the generation function 100a of the processing circuit 100 selects one element from the zeroth-generation reactant list $X_0$ and extracts the element $x_{02}$="CH$_4$" as a first element $x_m$. As another example, at step S220, the generation function 100a of the processing circuit 100 selects one element from the first-generation reactant list $X_1$ and extracts the element $x_{12}$="C$_2$H$_5$COOH" as a first element $x_m$.

Subsequently, at step S230, the generation function 100a of the processing circuit 100 selects one element from the pth-generation reactant list $X_p$ and extracts the selected element as a second element $x_n$. For example, when p=1, at step S230, the generation function 100a of the processing circuit 100 selects one element from the first-generation reactant list $X_1$ and extracts the element $x_{11}$="CH$_3$COOH" as a second element $x_n$. In this way, at step S220 and step S230, the generation function 100a of the processing circuit 100 extracts one or more compounds from the reactant list.

The generation function 100a of the processing circuit 100 repeats the process at step S220 to step S280 for various first elements $x_m$ and second elements $x_n$.

In this iterative process, the processing circuit 100 may perform the process at step S220 to step S280 for all combinations of first element $x_m$ and second element $x_n$ or conversely may perform the process at step S220 to step S280 for some combinations of possible combinations of first element $x_m$ and second element $x_n$.

Subsequently, at step S240 and step S250, the generation function 100a of the processing circuit 100 selects a partial structure subjected to a chemical reaction from the selected element.

At step S240, the generation function 100a of the processing circuit 100 extracts a first partial structure $y_m$ from the first element $x_m$ extracted at step S220. For example, when the first element $x_m$ extracted at step S240 is "C$_2$H$_5$COOH", this structure matches a structure in the form of "R—COOH", and then at step S240, the generation function 100a of the processing circuit 100 extracts a first partial structure $y_m$ as $y_m$="COOH". As another example of extraction of a partial structure, when the first element $x_m$ extracted at step S240 is "C$_2$H$_5$COOH", this structure matches a structure in the form of "R—H", and then at step S240, the generation function 100a of the processing circuit 100 extracts a first partial structure $y_m$ as $y_m$="H".

Similarly, at step S250, the generation function 100a of the processing circuit 100 extracts a second partial structure $y_n$ from the second element $x_n$ extracted at step S240.

The generation function 100a of the processing circuit 100 repeats the process at step S240 to step S280 for various first partial structures $y_m$ and second partial structures $y_n$.

Subsequently, the generation function 100a of the processing circuit 100 reads the chemical reaction list 110c from the storage unit 120 and determines whether the structure extracted at step S240 and step S250 is included in a chemical reaction listed in the chemical reaction list 110c. If the first partial structure $y_m$ and the second partial structure $y_n$ do not match the chemical reaction list (No at step S260), the process at step S240 to step S280 is repeated for new first partial structure $y_m$ and second partial structure $y_n$. On the other hand, if the first partial structure $y_m$ and the second partial structure $y_n$ match the chemical reaction list (Yes at step S260), the process proceeds to step S265. For example, when the first partial structure $y_m$ is "COOH" and the second partial structure $y_n$ is "H", these partial structures match the chemical reaction list {"$X_1$—CO—$X_2$", {"$X_1$—COOH", "$X_2$—H"}}. In such a case, therefore, the generation function 100a of the processing circuit 100 determines that a new compound can be produced by the chemical reaction, and the process proceeds to step S265.

In this way, the generation function 100a of the processing circuit 100 extracts a chemical reaction in which one or more compounds extracted at steps S220 and S230 are reactants, from the chemical reaction list 110c.

Subsequently, at step S265, the generation function 100a of the processing circuit 100 reads the prohibitive reaction list 110d from the storage unit 120 and determines whether the first partial structure $y_m$ extracted at step S240 and the second partial structure $y_n$ extracted at step S250 match a prohibition rule. If the first partial structure $y_m$ and the second partial structure $y_m$ match the prohibition rule (Yes at step S265), the processing circuit 100 does not perform a new process for this combination of partial structures and repeats the process at step S240 to step S280 for new first partial structure $y_m$, and second partial structure $y_n$. For example, when the first partial structure $y_m$ is "—COOH" and the second partial structure $y_n$ is "—CO—$CH_2$—CO—", these partial structures match the prohibitive reaction list {"$X_2$—CO—$CHX_1$—CO—$X_3$", {"$X_1$—COOH", "$X_2$—CO—$CHX_1$—CO—$X_3$"}}. In such a case, therefore, the generation function 100a of the processing circuit 100 determines that the new compound produced by the chemical reaction has no commercial value, and the processing circuit 100 does not perform a new process for this combination of partial structures and repeats the process at step S240 to step S280 for new first partial structure $y_m$ and second partial structure $y_n$. On the other hand, if the first partial structure $y_m$ and the second partial structure $y_n$ do not match the prohibition rule (No at step S265), the process proceeds to step S270, and the resultant product is added to the product list $Y_p$.

In this way, the generation function 100a of the processing circuit 100 produces the product list $Y_p$ further based on the prohibition rule. In the foregoing example, the prohibition rule is defined based on chemical reactions, that is, the prohibition rule is a rule that defines a chemical reaction excluded from the chemical reaction list at step S260. However, the embodiments are not limited thereto. That is, the prohibition rule may be defined based on products or reactants. In other words, the prohibition rule may be a rule that defines a product excluded from the product list $Y_p$ or a reactant corresponding to the product excluded from the product list $Y_p$. The embodiments are not limited to the foregoing examples, and the generation function 100a of the processing circuit 100 may define the product list $Y_p$, based on a permission rule that is a rule defining a chemical reaction incorporated into the chemical reaction list, rather than the prohibition rule that is a rule defining a chemical reaction excluded from the chemical reaction list.

Subsequently, at step S270, the generation function 100a of the processing circuit 100 produces a product $y_{mn}$ based on the chemical reaction list. For example, when the first element $x_m$ is "$C_2H_5COOH$", the second element $x_n$ is "$CH_4$", the first partial structure $y_n$ is "—COOH", the second partial structure $y_m$ is "—H", and the chemical reaction list is {"$X_1$—CO—$X_2$", {"$X_1$—COOH", "$X_2$—H"}}, the product $y_{mn}$ produced by the generation function 100a of the processing circuit 100 is "$C_2H_5$—CO—$CH_3$".

Subsequently, at step S275, the generation function 100a of the processing circuit 100 determines whether the product $y_{mn}$ produced at step S270, that is, the compound serving as a candidate for the product list $Y_p$ is included in a product list previously produced, that is, a compound already produced in the previous process. If the generation function 100a of the processing circuit 100 determines that the product $y_{mn}$ produced at step S270 is included in a product list previously generated, that is, if it is determined that the product $y_{mn}$ is a compound already produced in the previous process (Yes at step S275), the processing circuit 100 does not include the product $y_{mn}$ in the pth-generation product list $Y_p$ and repeats the process at steps S240 to S280 for new first partial structure $y_m$ and second partial structure $y_n$.

On the other hand, if the generation function 100a of the processing circuit 100 determines that the product $y_{mn}$ produced at step S270 is not a compound already produced in the previous process (No at step S275), the process proceeds to step S280, and the processing circuit 100 adds the product $y_{mn}$ to the pth-generation product list $Y_p$. In this way, the generation function 100a of the processing circuit 100 adds the product $y_{nm}$ of the chemical reaction extracted at step S260 and produced at step S270 to the list of product $Y_p$ made of one or more compounds.

The generation function 100a of the processing circuit 100 repeats the process at step S240 to S280 for various first partial structures $y_m$ and second partial structures $y_n$ while changing the first partial structure $y_m$ and the second partial structure $y_n$ for given first element $x_m$ and second element $x_n$. The generation function 100a of the processing circuit 100 also repeats the process at step S220 to step S280 for various first elements $x_m$ and second elements $x_n$.

The embodiments are not limited to the foregoing example.

In FIG. 6, the chemical reaction used for production of a compound is a chemical reaction that produces one product from two reactants (the number of dimensions of the reaction is two). However, the embodiments are not limited thereto. As an example, the chemical reaction used for production of a compound may be a chemical reaction that produces one product from three reactants (the number of dimensions of the reaction is three), may be a chemical reaction that produces two products from one reactant, or may be a chemical reaction that produces one product from one reactant where the product is different from the reactant.

For example, a case where a chemical reaction used for production of a compound is a chemical reaction that produces one product from three reactants will be described. In such a case, instead of step S220 to step S230, the generation function 100a of the processing circuit 100 extracts a first element $x_{m1}$ from any one reactant list among the zeroth- to pth-generation reactant lists $X_0$ to $X_p$, extracts a second element $x_{m2}$ from any one reactant list among the zeroth- to pth-generation reactant lists $X_0$ to $X_p$, and extracts a third element $x_{m3}$ from the pth-generation reactant list $X_p$. Furthermore, instead of step S240 to step S250, the generation function 100a of the processing circuit 100 extracts a first partial structure $y_{m1}$ from the first element $x_{m1}$, extracts a second partial structure $y_{m2}$ from the second element $x_{m2}$, and extracts a third partial structure $y_{m3}$ from the third element $x_{m3}$. The generation function 100a of the processing circuit 100 performs a similar process for various first partial structures $y_{m1}$, second partial structures $y_{m2}$, and third partial structures $y_{m3}$ for a given combination of first element $x_{m1}$, second element $x_{m2}$, and third element $x_{m3}$, and performs these processes for various combinations of first element $x_{m1}$, second element $x_{m2}$, and third element $x_{m3}$.

For example, a case where a chemical reaction used for production of a compound is a chemical reaction that produces two products from one reactant will be described. In such a case, instead of step S220 to step S230, the generation function 100a of the processing circuit 100 extracts an element $x_m$ from the pth-generation reactant list $X_p$. Furthermore, instead of step S240 to step S250, the generation function 100a of the processing circuit 100 extracts a partial structure $y_m$ from the element $x_m$. The generation function 100a of the processing circuit 100 acquires a chemical reaction matched with the partial structure $y_m$ from the chemical reaction list 110c at step S260, checks a prohibition rule at step S265, and thereafter produces two products $y_{m:1}$, $y_{m:2}$ based on the chemical reaction list at step S270. At step S275, it is determined whether each of these products is a compound already produced and thereafter, if not a compound already produced, adds the product to the pth-generation product list $Y_p$ at step S280.

These processes can be easily generalized when a chemical reaction used for production of a compound is a chemical reaction that produces r products from q reactants.

The chemical reaction used for production of a compound may be, for example, a chemical reaction that produces one product from one reactant, such as a chemical reaction that produces a product "R—Br" from a reactant "R—OH". This chemical reaction can be represented, for example, by {{"R—Br"}, {"R—OH"}}.

In the embodiment described above, the processing circuit 100 having the generation function 100a extracts a first element $x_m$ from the zeroth-generation to pth-generation reactant lists $X_0$ to $X_p$ at step S220 and extracts a second element $x_n$ from the pth-generation reactant list $X_p$ at step S230. However, the embodiments are not limited thereto. For example, the processing circuit 100 having the generation function 100a may extract a second element $x_n$ from the zeroth-generation to pth-generation reactant lists $X_0$ to $X_p$ also at step S230.

A case where the reactant list $X_p$ includes a special compound $x_{null}$ as an element in FIG. 6 will now be described. The special compound $x_{null}$ is a special element indicating an operation of not selecting a compound, and selecting the special compound $x_{null}$ is treated as no compound being selected.

For example, a case where the reactant list $X_p$ is a list of n+1 elements including n elements $x_1, x_2 \ldots x_n$ that are normal compounds and the special compound $x_{null}$, and three elements are extracted from this list where overlapping is allowed will be discussed. When three compounds other than the special compound $x_{null}$, such as $x_k$, $x_l$, $x_m$, are extracted, the generation function 100a of the processing circuit 100 extracts a three-dimensional reaction with three reactants $x_k$, $x_l$, $x_m$. A case where $x_{null}$ is extracted once and two compounds other than $x_{null}$, such as $x_k$, $x_l$, are extracted is treated as one compound not being selected, and the generation function 100a of the processing circuit 100 extracts a two-dimensional reaction with two reactants $x_k$, $x_l$. A case where $x_{null}$ is extracted twice and one compound other than $x_{null}$, such as $x_k$, is extracted is treated as two compounds not being selected, and the generation function 100a of the processing circuit 100 extracts a one-dimensional reaction with one reactant $x_k$. In this way, by making a list of n+1 elements including n compounds $x_1, x_2 \ldots x_n$ and the special compound $x_{null}$ as the reactant list $X_p$ and extracting d elements from this list, where overlapping is allowed, the generation function 100a of the processing circuit 100 can exhaustively count up chemical reactions in which the number of reactants is 1 to d, that is, the dimensions of reaction are equal to or smaller than d. That is, the reactant list $X_p$ includes an operation of not selecting a compound as the element $x_{null}$, and the generation function 100a of the processing circuit 100 extracts the element $x_{null}$ from the reactor list $X_p$ instead of extracting a compound, whereby compounds obtained by a chemical reaction involving a smaller number of reactants than when the element $x_{null}$ is not extracted can be added to the product list $Y_p$.

The reactant list $X_p$ may include an operation of converting a structure of a certain compound into a compound different from the original compound, as an element. Here, an example of the "operation of converting a structure of a certain compound into a compound different from the original compound" is an operation such as intramolecular reaction, isomerization, and substitution of a functional group.

Figure 7:
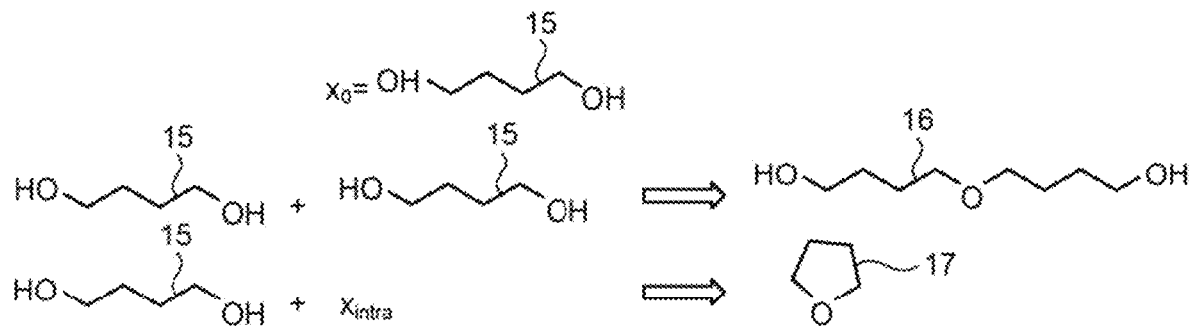
FIG. 7 is a diagram illustrating a process performed by the chemical structure generating device according to the first embodiment.

Such an operation will be described with reference to FIG. 7, taking an intramolecular reaction as an example. FIG. 7 is a diagram illustrating a process performed by the chemical structure generating device according to the first embodiment.

First, a normal chemical reaction that is not an intramolecular reaction will be described. A case where the compound $x_0$ included in the reactant list $X_p$ is a compound 15 illustrated in FIG. 7 will be discussed. Here, in the case of a normal chemical reaction that is not an intramolecular reaction, as illustrated in the middle section of FIG. 7, two molecules of the compound 15 come together to produce a compound 16. In such a case, the reactants of the chemical reaction are represented as {"compound 15", "compound 15"}, the product of the chemical reaction is represented as "compound 16", and the chemical reaction is represented as {{"compound 16"}, {{"compound 15", "compound 15"}}.

Next, a case where an intramolecular reaction is included will be discussed. When an intramolecular reaction exists, as illustrated in the lower section of FIG. 7, an intramolecular reaction occurs in one molecule of the compound 15 to produce a compound 17. In such a case, although the reactant of the chemical reaction can be represented as "compound 15", the product of the chemical reaction can be represented as "compound 17", and the chemical reaction can be represented as {"compound 17", "compound 15"}, the processing circuit 100 having the generation function 100a may treat the operation $x_{intra}$ of performing an intramolecular reaction as an element included in the reactant list $X_p$. Specifically, the processing circuit 100 having the generation function 100a represents the reactant of the reaction as {"compound 15", $x_{intra}$} using the special element corresponding to the operation $x_{intra}$ of performing an intramolecular reaction, the product of the chemical reaction as "compound 17", and the chemical reaction as {{"compound 17"}, {"compound 15", $x_{intra}$}} and then performs the process illustrated in FIG. 6. The processing circuit 100 having the generation function 100a treats the operation $x_{intra}$ of performing an intramolecular reaction as an element included in the reactant list $X_p$ to add a compound obtained by performing an intramolecular reaction on any compound in the reactant list to the product list $Y_p$. As indicated by this example, by treating the operation on a molecule as an element included in a set of molecule candidates, the processing circuit 100 having the generation function 100a can systematically generate molecule candidates obtained by an operation such as an intramolecular reaction.

The product $y_{nm}$ produced by the generation function 100a of the processing circuit 100 at step S270 is typically some kind of chemical structure (compound). However, the embodiments are not limited thereto. For example, at step S270, the generation function 100a of the processing circuit 100 may generate the special compound $x_{null}$ or $x_{intra}$ as a product $y_{nm}$. For example, when all the elements selected as reactants are $x_{null}$, the generation function 100a of the processing circuit 100 generates $x_{null}$ as a product at step S270. When all the elements selected as reactants are $x_{intra}$, the generation function 100a of the processing circuit 100 generates $x_{intra}$ as a product at step S270. When only a special compound is selected as a reactant, the process of step S240, step S250, step S260, step S265, step S275, or the like in FIG. 6 is not necessarily performed.

As described above, in the chemical structure generating device 1 according to the first embodiment, the generation function 100a of the processing circuit 100 produces a product list including one or more compounds based on a reactant list including one or more compounds and a chemical reaction list, the control function 100b applies the product list as a new reactant list and allows the generator to produce a new product list based on the new reactant list and the chemical reaction list. This process enables efficient generation of molecular structures appropriate for use as training data for machine learning, molecular structures having commercial value, and molecular structures that can be actually manufactured.

Second Embodiment

In a second embodiment, a chemical structure generating device will be described that generates molecular structures having commercial value even more efficiently by assigning numerical information to each of the compounds serving as candidates and performing control, as a method of efficiently generating molecular structures having commercial value.

In the second embodiment, the chemical structure generating device 1 assigns numerical information to each of the compounds serving as candidates based on the numerical information list 110e and performs control based on the numerical information. As used herein the numerical information assigned to each of the compounds is, for example, information indicating a cost necessary for producing the compound.

In a typical case, the numerical information is assigned to each compound.

For example, a case where the pth-generation reactant list $X_p$ includes compounds $x_1, x_2, \ldots x_n$, and the costs for producing the compounds $x_1, x_2, \ldots, x_n$ are $w_1, w_2, \ldots, w_n$, respectively, will be discussed. In this case, the elements in the numerical information list $W_p$ corresponding to the pth-generation reactant list are $w_1, w_2, \ldots w_n$.

The processing circuit 100 having the generation function 100a may integrate the reactant list 110a and the numerical information list 110e to produce one compound list $X'_p = \{x_1(w_1), x_2(w_2), \ldots x_n(w_n)\}$ in which numerical information is set as an attribute for each compound.

The generation function 100a of the processing circuit 100 calculates the numerical information for each compound. Specifically, the processing circuit 100 having the generation function 100a provides known numerical information as numerical information for a compound whose numerical information is known and, for numerical information of any other compound, recursively defines numerical information based on numerical information of reactants of the compound, based on a synthesis pathway of the compound, until reaching a compound with known numerical information.

Figure 8:
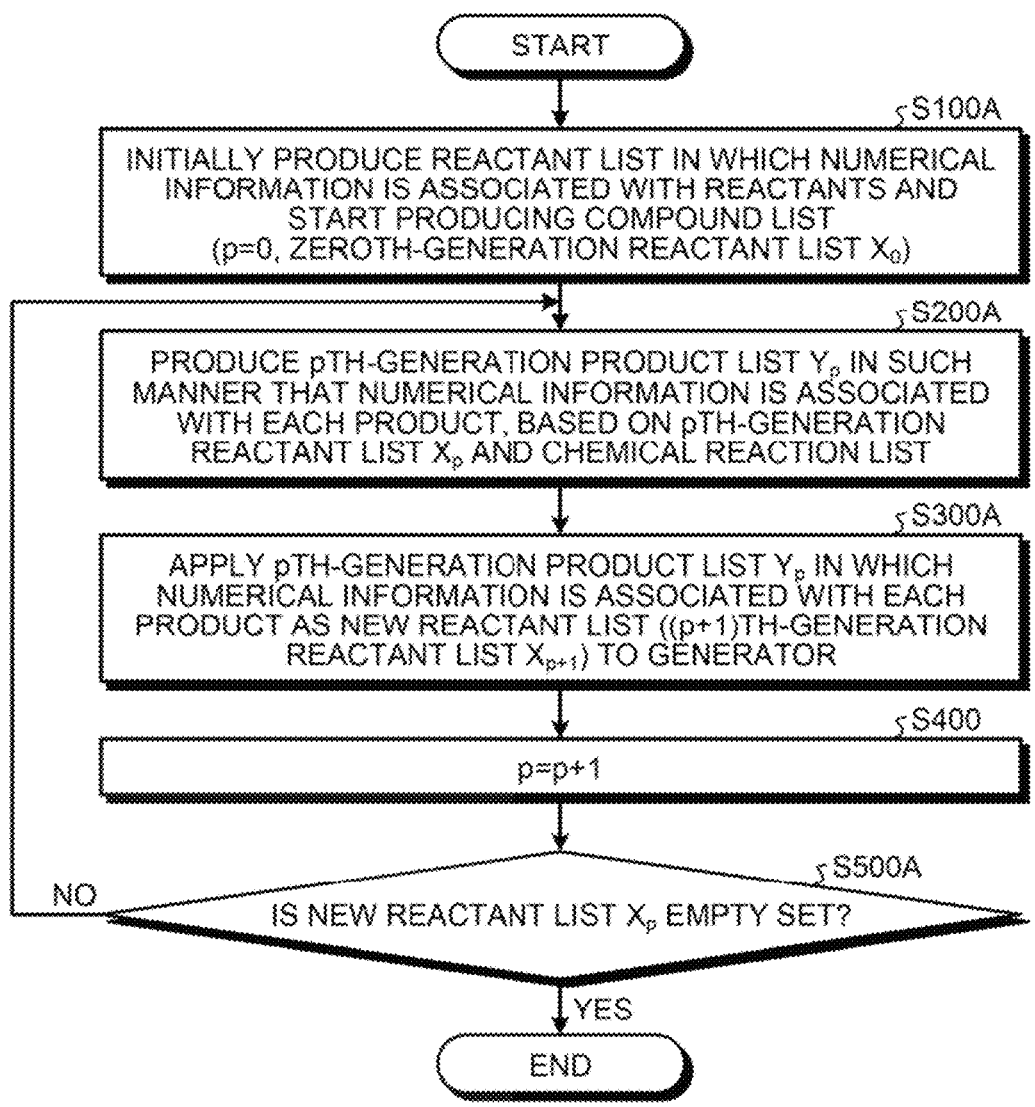
FIG. 8 is a flowchart illustrating a process performed by the chemical structure generating device according to a second embodiment.

Such a process will be specifically described with reference to FIG. 8 and FIG. 9. FIG. 8 and FIG. 9 are flowcharts illustrating a process performed by the chemical structure generating device according to the second embodiment. FIG. 8 is a flowchart illustrating the entire process, and FIG. 9 is a flowchart illustrating the process at step S200A in FIG. 8. A description of the process in FIG. 8 and FIG. 9 already explained in the first embodiment will not be repeated.

First of all, the generation function 100a of the processing circuit 100 starts producing a compound list (step S100A). The generation function 100a of the processing circuit 100 produces a pth-generation reactant list $X_p$ and a numerical information list $W_p$ corresponding to the reactants of the pth-generation reactant list $X_p$, as a compound list and a numerical information list (a list of cost information), respectively, while incrementing p, based on the zeroth-generation reactant list $X_0$ and the numerical information list $W_0$ corresponding to the reactants, where p=0 in an initial state. As an example, the processing circuit 100 having the generation function 100a initially produces a reactant list $X_0 = \{x_1, x_2, \ldots x_n\}$ and a list of information such as numerical information (cost information) $W_0 = \{w_1, w_2, \ldots, w_n\}$ and initially produces a reactant list $X_0' = \{x_1(w_1), x_2(w_2), \ldots, x_n(w_n)\}$ in which numerical information is associated with a reactant, based on these lists, to start producing a compound list.

Subsequently, the generation function 100a of the processing circuit 100 produces a pth-generation product list $Y_p$ as a product list 110b, based on the pth-generation reactant list $X_p$ that is the reactant list 110a and the chemical reaction list 110c that is a list of chemical reactions. In addition to this process, the generation function 100a of the processing circuit 100 also calculates a numerical information list $W_p$ corresponding to the products of the pth-generation product list $Y_p$. That is, the processing circuit 100 having the generation function 100a produces the pth-generation product list $Y_p$ in such a manner that numerical information is associated with each product (step S200A). The detail of the process at step S200A will be described later with reference to FIG. 9.

Subsequently, the control function 100b of the processing circuit 100 applies the pth-generation product list $Y_p$ and the numerical information list $W_p$ corresponding to the products, as a new reactant list (the (p+1)th-generation reactant list $X_{p+1}$) and a new numerical information list $W_{p+1}$, respectively, to the computer program related to the generation function 100a (step S300A). In this way, the processing circuit 100 having the control function 100b applies the pth-generation product list $Y_p$ in which numerical information is associated with each product, as a new reactant list (the (p+1)th-generation reactant list $X_{p+1}$), to the computer program related to the generation function 100a.

Subsequently, the control function 100b of the processing circuit 100 increments the value of p by 1 (step S400). Subsequently, the control function 100b of the processing circuit 100 determines whether the new reactant list $X_p$ is an empty set. In the second embodiment, the processing circuit 100 having the generation function 100a performs control using the numerical information list $W_p$ and restricts compounds to be produced. Therefore, as p increases, the number of elements of a new reactant list $X_p$ naturally decreases. The processing circuit 100 having the control function $100b$ therefore can set an end point of the process involving p, at p in which a new reactant list $X_p$ is an empty set.

That is, when a new reactant list $X_p$ is an empty set (Yes at step S500A), the process ends, and if a new reactant list $X_p$ is not an empty set (No at step S500A), the process returns to step S200A. Such a stop condition of the process enables efficient generation of a commercially valuable compound, for example, whose cost is smaller than a given threshold.

The detail of the process at step S200A will now be described with reference to FIG. 9. In FIG. 9, the numerical information list $W_p$ corresponding to the reactants is information representing the costs as a product of the reactants.

In FIG. 9, a chemical reaction used in production of a product list is a chemical reaction that produces one product from two reactants, in the same manner as in FIG. 6. However, as already mentioned, the embodiment can be applied similarly even when the number of reactants or products is different from the above.

First of all, at step S210A, the generation function $100a$ of the processing circuit 100 starts producing a pth-generation product list $Y_p$ in the product list $110b$. Immediately after the generation function $100a$ of the processing circuit 100 starts producing the product list $Y_p$, the product list $Y_p$ is an empty set.

At step S220A, the generation function $100a$ of the processing circuit 100 selects one element from any one reactant list among the zeroth-generation reactant list $X_0$, the first-generation reactant list $X_1$, the second-generation reactant list $X_2$, ... and the pth generation-reactant list $X_p$ and extracts the selected element as a first element $x_m$, in the same manner as in the first embodiment.

Subsequently, at step S230A, the generation function $100a$ of the processing circuit 100 selects one element from the pth-generation reactant list $X_p$ and extracts the selected element as a second element $x_n$. In this way, at step S220 and step S230, the generation function $100a$ of the processing circuit 100 extracts one or more compounds from the reactant list.

The generation function $100a$ of the processing circuit 100 repeats the process at step S220A to step S280A for various first elements $x_m$ and second elements $x_n$.

Subsequently, at step S231, the generation function $100a$ of the processing circuit 100 calculates the reactant cost (the sum of raw material costs) for a reaction including the first element $x_m$ selected at step S220A and the second element $x_n$ selected at step S230A. Here, if the product cost, which is the sum of the reactant cost (the sum of raw material costs) and the cost for performing a chemical reaction, exceeds a permissible cost at a point of time of the sum of raw material costs, the cost for a chemical reaction need not be considered and the product cost exceeds the maximum permissible cost. The processing circuit 100 having the generation function $100a$ therefore performs a pruning process at step S232 before entering a loop for partial structures.

Specifically, if the reactant cost, for example, the sum $w_m + w_n$ of the cost $w_m$ for the first element $x_m$ selected at step S220A and the cost $w_n$ for the second element $x_n$ selected at step S230A exceeds a permissible cost (No at step S232), the processing circuit 100 having the generation function $100a$ determines that the first element $x_m$ and the second element $x_n$ selected at step S220A and step S230 are not appropriate elements and repeats the process at step S220A to step S280A for new first element $x_m$ and second element $x_n$. On the other hand, if the reactant cost, for example, the sum $w_m + w_n$ of the cost $w_m$ for the first element $x_n$ selected at step S220A and the cost $w_n$ for the second element $x_n$ selected at step S230A does not exceed a permissible cost (Yes at step S232), the process proceeds to step S240.

Subsequently, at step S240 and step 3250, the generation function $100a$ of the processing circuit 100 selects a partial structure subjected to a chemical reaction from the selected element. For example, at step S240, the generation function $100a$ of the processing circuit 100 extracts a first partial structure $y_m$ from the first element $x_m$ extracted at step S220. Similarly, at step S240, the generation function $100a$ of the processing circuit 100 extracts a second partial structure $y_n$ from the second element $x_n$ extracted at step S230.

The generation function $100a$ of the processing circuit 100 repeats the process at step S240 to step S280A for various first partial structures $y_m$ and second partial structures $y_n$.

Subsequently, the generation function $100a$ of the processing circuit 100 reads the chemical reaction list $110c$ from the storage unit 120 and determines whether the structures extracted at step S240 and step S250 are included in a chemical reaction listed in the chemical reaction list $110c$. If the first partial structure $y_m$ and the second partial structure $y_n$ do not match the chemical reaction list (No at step S260), the process at step S240 to step S280A is repeated for new first partial structure $y_m$ and second partial structure $y_n$. On the other hand, if the first partial structure $y_m$ and the second partial structure $y_n$ match the chemical reaction list (Yes at step S260), the process proceeds to step S270.

In this way, the generation function $100a$ of the processing circuit 100 extracts a chemical reaction in which one or more compounds extracted at steps S220A and S230A are reactants, from the chemical reaction list $110c$.

Subsequently, at step S270, the generation function $100a$ of the processing circuit 100 produces a product $y_{mn}$ based on the chemical reaction list.

Subsequently, at step S275, the generation function $100a$ of the processing circuit 100 determines whether the product $y_{mn}$ produced at step S270, that is, the compound serving as a candidate for the product list $Y_p$ is included in a product list previously produced, that is, whether it is a compound already produced in the previous process. If the generation function $100a$ of the processing circuit 100 determines that the product $y_{mn}$ produced at step S270 is included in a product list previously produced, that is, if it is determined that the product $y_{mn}$ is a compound already produced in the previous process (Yes at step S275), the processing circuit 100 does not include the product $y_{mn}$ in the pth-generation product list $Y_p$ and repeats the process at steps S240 to S280 for new first partial structure $y_m$ and second partial structure $y_n$.

On the other hand, if the generation function $100a$ of the processing circuit 100 determines that the product $y_{mn}$ produced at step S270 is not a compound already produced in the previous process (No at step S275), the process proceeds to step S271A.

At step S271A, the processing circuit 100 having the generation function $100a$ calculates the production cost $w_{mn}$ for the product $y_{mn}$ produced at step S270. Here, the production cost $w_{mn}$ is the sum of the sum $w_m + w_n$ of reactant costs and the cost $z_{mn}$ for a chemical reaction. Specifically, the processing circuit 100 having the generation function $100a$ produces numerical information corresponding to each of compounds $y_{mn}$ serving as candidates for the product list $Y_p$, using the sum $w_m + w_n$ of the costs for reactants that are raw materials of a compound serving as a candidate and the cost $z_{mn}$ for a chemical reaction $\{y_{mn}, \{x_m, x_n\}\}$ producing the compound $y_{mn}$ serving as a candidate from the reactants. Here, the processing circuit 100 having the generation function 100a acquires the cost $z_{mn}$ for the chemical reaction from the chemical reaction list 110c. The chemical structure generating device 1 stores the chemical reaction and the cost for the chemical reaction into the storage unit 120 in association with the chemical reaction list 110c.

Subsequently, at step S272, the generation function 100a of the processing circuit 100 determines whether the production cost $w_{mn}$ for the product $y_{mn}$ calculated at step S271A is equal to or lower than the maximum permissible cost $c_{max}$. If the production cost $w_{mn}$ is not equal to or lower than the maximum permissible cost $c_{max}$ (No at step S272), the product $y_{mn}$ is not added to the product list $Y_p$, and the process at step S240 to step S280A is repeated for new first partial structure $y_m$ and second partial structure $y_n$. On the other hand, if the production cost $w_{mn}$ is equal to or lower than the maximum permissible cost $c_{max}$ (Yes at step S272), the process proceeds to step S280A.

In this way, when producing a compound $y_{mn}$ serving as a candidate for the product list $Y_p$, the processing circuit 100 having the generation function 100a calculates the production cost $w_{mn}$ that is numerical information corresponding to each compound $y_{mn}$ serving as a candidate at step S271A and determines whether to include the compound $y_{mn}$ serving as a candidate in the product list $Y_p$, based on the calculated production cost $w_{mn}$ that is numerical information at step S272.

That is, each of the reactants included in the reactant list $X_p$ is associated with information representing the cost of the reactant. The processing circuit 100 having the generation function 100a calculates the cost $w_{mn}$ of the compound $y_{mn}$ serving as a candidate for the product list $Y_p$, based on the information representing the cost of the reactant at step S271A, compares the calculated cost $w_{mn}$ of the compound $y_{mn}$ serving as a candidate for the product list $Y_p$ with the maximum permissible cost $c_{max}$ that is a preset threshold at step S272. If the cost $w_{mn}$ exceeds the maximum permissible cost $c_{max}$, which is a threshold (No at step S272), the processing circuit 100 does not include the compound $y_{mn}$ serving as a candidate in the product list $Y_p$.

At step S280A, the processing circuit 100 adds the product $y_{mn}$ to the pth-generation product list $Y_p$ and adds the production cost $w_{mn}$ of the product $y_{mn}$ to the pth-generation numerical information list $W_p$. In this way, the generation function 100a of the processing circuit 100 adds a product to the product list $Y_p$ including one or more compounds.

The generation function 100a of the processing circuit 100 repeats the process at step S240 to S280A for various first partial structures $y_m$ and second partial structures $y_n$ while changing the first partial structure $y_m$ and the second partial structure $y_n$ for given first element $x_m$ and second element $x_n$. The generation function 100a of the processing circuit 100 also repeats the process at step S220A to step S280A for various first elements $x_m$ and second elements $x_n$.

The embodiments are not limited to the foregoing examples.

In the embodiment described above, the numerical information list $W_p$ corresponding to each compound is information representing the cost of the compound. However, the embodiments are not limited thereto. For example, the numerical information list $W_p$ corresponding to each compound may be a score defined for each compound. As an example, the processing circuit 100 having the generation function 100a may determine comprehensive commercial usability for each compound, based on not only mere prices of raw materials but also various factors such as technical level of difficulty in handling, availability of raw materials, and market demands to set a score for each compound, and may preferentially add the one having a high score or exceeding a certain threshold to the next-generation reactant list. Here, the score set for each compound may be such a score that a higher score indicates a more desirable compound, or conversely may be such a score that a lower score indicates a more desirable compound. As an example of the numerical information list $W_p$ corresponding to each compound, information on physical properties of the compound, such as molecular weight, vapor pressure, boiling point, melting point, dipole moment, and oil-water partition coefficient (for example, log P), may be used.

In the embodiment described above, when producing a compound serving as a candidate for the product list $Y_p$, the processing circuit 100 having the generation function 100a further calculates numerical information corresponding to each compound serving as a candidate and determines whether to include the compound serving as a candidate in the product list $Y_p$, based on the calculated numerical information. However, the embodiments are not limited thereto. For example, when producing a compound serving as a candidate for the product list $Y_p$, the processing circuit 100 having the generation function 100a may further calculate information that is not numerical information corresponding to each compound serving as a candidate and may determine whether to include the compound serving as a candidate in the product list $Y_p$, based on the calculated information. Examples of the information that is not numerical information include information as to whether a particular substituent is included and information such as hazardous materials classification by a public period. In such a case, for example, the processing circuit 100 having the generation function 100a excludes, from the product list $Y_p$, a compound serving as a candidate for the product list that includes a particular substituent or is classified in a particular hazardous material class.

In the iterative process for the first element $x_m$ and the second element $x_n$ in the flowchart in FIG. 9 described above, selection of the first element $x_m$ and the second element $x_n$ is performed successively, irrespective of the content of the numerical information list $W_p$ of the compounds. However, the embodiments are not limited thereto. The processing circuit 100 having the generation function 100a may search for a first element $x_m$ and a second element $x_n$ in accordance with a priority order based on the numerical information of each compound, for example, in order of increasing cost or in order of decreasing score and may generate a candidate $y_{mn}$ for the product list $Y_p$.

In the embodiments, the cost of a compound is not limited to information merely indicating the price of the compound and may include a variety of costs other than price, such as the difficulty level of safety control and the availability or stability of raw materials.

The numerical information in the embodiments is not limited to numerical information in the form of scalar quantity but may be numerical information in the form of vector quantity or tensor quantity, if necessary.

In the embodiment described above, the processing circuit 100 successively produces a pth-generation product list $Y_p$ based on the zeroth-generation reactant list $X_0$. That is, in the embodiment described above, one reactant list $Y_p$ is produced based on one initial list named the zeroth-generation reactant list $X_0$. However, the embodiments are not limited thereto. A plurality of reactant lists respectively corresponding to a plurality of initial lists may be produced based on the initial lists.

For example, a case where when a certain compound (this compound itself is not necessarily a target to be computed by the present compound generating device) requires two or more raw material groups (for example, group A, group B, group C . . . ), respective compound lists of the raw material groups (a compound list of group A, a compound list of group B, a compound list of group C . . . ) are produced within a permissible cost will be discussed.

In this case, for example, the generation function 100a of the processing circuit 100 produces a pth-generation compound list $Y_{p,A}$ for compounds in group A based on the zeroth-generation reactant list $X_{0,A}$ for compounds in group A, produces a pth-generation compound list $Y_{p,B}$ for compounds in group B based on the zeroth-generation reactant list $X_{0,B}$ for compounds in group B, and produces a pth-generation compound list $Y_p$, c for compounds in group C based on the zeroth-generation reactant list $X_{0,c}$ for compounds in group C.

First, a first case where a permissible cost is set for each of the raw material groups will be discussed. In such a case, the generation function 100a of the processing circuit 100 may perform the process already explained for each of the raw material groups by setting a permissible cost set for each raw material group as the maximum permissible cost $c_{max}$ at step S272 in FIG. 9. For example, a case where compound lists of two kinds of raw material groups, namely, group A and group B are produced will be discussed, where the entire permissible cost c is given and the ratio between the permissible cost for group A and the permissible cost for group B is set to 8:2. In this case, the processing circuit 100 performs the process for each group by setting a permissible cost $c_{max}=0.8$ c for group A and a permissible cost $c_{max}=0.2$ c for group B.

Next, a second case where the permissible cost is set for the whole of the raw material groups, rather than each of the raw material groups, will be discussed. In such a case, the generation function 100a of the processing circuit 100 performs the respective processes concurrently or alternately for the raw material groups, and then determines whether the production cost of a product is equal to or lower than the maximum permissible cost by referring to information on the permissible cost of the compound list produced in the other raw material group at the process at step S272 in FIG. 9. As an example, in the process at step S272 in the process of producing a compound list of group A, if the sum of the production cost of a product produced at present and the minimum value of the production cost in the compound list of group B exceeds the permissible cost of the whole, the generation function 100a of the processing circuit 100 does not add the product to the product list.

By performing the process described above, the processing circuit 100 can produce compound lists for two or more raw material groups simultaneously and concurrently.

In this way, in the second embodiment, the processing circuit 100 assigns numerical information to each of the compounds serving as candidates and performs control of chemical structure generation. This configuration enables even more efficient generation of molecular structures having commercial value and suitable for use as training data for machine learning.

In this way, the embodiments of the present invention can efficiently generate molecular structures suitable for use as training data for machine learning.

The embodiments of the present invention are provided only by way of example and susceptible to various modifications and changes.

For the foregoing embodiments, the following note is disclosed as selective features of the present invention.

Note

A data processing system comprising:
 a database having at least one list of a reactant list including one or more compounds and a product list including one or more compounds; and
 a chemical structure generating device,
 the chemical structure generating device including
  a generator configured to produce the product list based on the reactant list and a chemical reaction list, and
  a controller configured to apply the product list as a new reactant list to the generator, update the database, and allow the generator to produce a new product list based on the new reactant list and the chemical reaction list.

According to the present invention, molecular structures suitable for use as training data for machine learning can be efficiently generated.

The methods, processes, and/or operations described herein may be performed by code or instructions to be executed by a computer, processor, controller, or other signal processing device. The computer, processor, controller, or other signal processing device may be those described herein or one in addition to the elements described herein. Because the algorithms that form the basis of the methods (or operations of the computer, processor, controller, or other signal processing device) are described in detail, the code or instructions for implementing the operations of the method embodiments may transform the computer, processor, controller, or other signal processing device into a special-purpose processor for performing the methods herein.

Also, another embodiment may include a computer-readable medium, e.g., a non-transitory computer-readable medium, for storing the code or instructions described above. The computer-readable medium may be a volatile or non-volatile memory or other storage device, which may be removably or fixedly coupled to the computer, processor, controller, or other signal processing device which is to execute the code or instructions for performing the method embodiments or operations of the apparatus embodiments herein.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A chemical structure generating device comprising:
 a processing circuit, including:
 a generator configured to produce a product list including one or more compounds, based on a reactant list including one or more compounds and a chemical reaction list; and
 a controller configured to apply the product list as a new reactant list to the generator, update a database having at least one list of the reactant list and the product list, and allow the generator to produce a new product list based on the new reactant list and the chemical reaction list,
 wherein numerical information is associated with each of the reactants, the numerical information associated with each of the reactants is information representing a cost of each of the reactants as a product, the generator produces numerical information corresponding to each of the compounds serving as the candidates, using a sum of a cost of the reactant that is a raw material of the compound serving as the candidate and a cost for a chemical reaction that produces the compound serving as the candidate from the reactant, information representing a cost of each of the reactants is associated with the reactant, the generator calculates a cost of a compound serving as a candidate for the product list, based on the information representing the cost of the reactant, and compares the calculated cost of the compound serving as the candidate for the product list with a preset threshold, wherein when the cost exceeds the threshold, the compound serving as the candidate is not included in the product list, and the processing circuit is configured to produce compound lists for two or more raw material groups simultaneously and concurrently.

2. The chemical structure generating device according to claim 1, wherein the generator extracts one or more compounds from the reactant list, extracts a chemical reaction in which the one or more compounds are reactants, from the chemical reaction list, and adds a product of the chemical reaction to the product list including the one or more compounds.

3. The chemical structure generating device according to claim 1, wherein the generator produces the product list, further based on a prohibition rule that is a rule defining a product excluded from the product list to be produced or a chemical reaction excluded from the chemical reaction list.

4. The chemical structure generating device according to claim 1, wherein the generator determines whether a compound serving as a candidate for the product list is included in a product list previously produced, and when determining that the compound serving as the candidate is included in the product list previously produced, the generator does not include the compound serving as the candidate in the product list.

5. The chemical structure generating device according to claim 1, wherein when producing compounds serving as candidates for the product list, the generator further calculates information corresponding to each of the compounds serving as the candidates and determines whether to include the compounds serving as the candidates in the product list, based on the calculated information.

6. The chemical structure generating device according to claim 1, wherein numerical information is associated with each of the reactants, and the generator generates a candidate for the product list in accordance with a priority order based on the numerical information.

7. The chemical structure generating device according to claim 1, wherein the reactant list includes an operation of not selecting a compound, as an element, and the generator extracts the element from the reactant list instead of extracting a compound and adds a compound obtained by a chemical reaction involving a smaller number of reactants than when the element is not extracted, to the product list.

8. The chemical structure generating device according to claim 1, wherein the reactant list includes an operation of converting a structure of a certain compound into a compound different from the certain compound, as an element.

9. The chemical structure generating device according to claim 1, wherein the generator treats an operation of performing an intramolecular reaction as an element included in the reactant list and adds a compound obtained by performing an intramolecular reaction on any compound in the reactant list, to the product list.

10. The chemical structure generating device according to claim 1, wherein the controller stores the product list produced by the generator into a storage unit as the database.

11. The chemical structure generating device according to claim 1, wherein at least a part of the database updated is used as training data in machine learning.

12. A non-transitory computer-readable medium storing a chemical structure generating program for causing a computer to perform:

a process using a processing circuit having a generator for producing a product list including one or more compounds, based on a reactant list including one or more compounds and a chemical reaction list;

a process using the processing circuit having a controller for applying the product list as a new reactant list to the generator;

a process using the controller for updating a database having at least one list of the reactant list and the product list;

a process using the controller to allow producing a new product list by the generator based on the new reactant list and the chemical reaction list;

a process of associating numerical information with each of the reactants, wherein the numerical information associated with each of the reactants is information representing a cost of each of the reactants as a product;

a process using the generator for producing numerical information corresponding to each of the compounds serving as the candidates, using a sum of a cost of the reactant that is a raw material of the compound serving as the candidate and a cost for a chemical reaction that produces the compound serving as the candidate from the reactant, wherein information representing a cost of each of the reactants is associated with the reactant;

a process using the generator for calculating a cost of a compound serving as a candidate for the product list, based on the information representing the cost of the reactant, and comparing the calculated cost of the compound serving as the candidate for the product list with a preset threshold, wherein when the cost exceeds the threshold, the compound serving as the candidate is not included in the product list; and a process using the processing circuit for producing compound lists for two or more raw material groups simultaneously and concurrently.

13. A chemical structure generating method, the chemical structure generating method comprising:

producing using a generator device of a processing circuit a product list including one or more compounds, based on a reactant list including one or more compounds and a chemical reaction list;

applying using a controller device of a processing circuit the product list as a new reactant list to the generator device;

updating using the controller device a database having at least one list of the reactant list and the product list;

using the controller to allow producing a new product list by the generator device based on the new reactant list and the chemical reaction list;

associating numerical information with each of the reactants, wherein the numerical information associated with each of the reactants is information representing a cost of each of the reactants as a product;

producing using the generator device numerical information corresponding to each of the compounds serving as the candidates, using a sum of a cost of the reactant that is a raw material of the compound serving as the candidate and a cost for a chemical reaction that produces the compound serving as the candidate from the reactant, and wherein information representing a cost of each of the reactants is associated with the reactant;

calculating using the generator a cost of a compound serving as a candidate for the product list, based on the information representing the cost of the reactant, and comparing the calculated cost of the compound serving as the candidate for the product list with a preset threshold, wherein when the cost exceeds the threshold, the compound serving as the candidate is not included in the product list; and producing with the processing circuit compound lists for two or more raw material groups simultaneously and concurrently.

14. The non-transitory computer-readable medium of claim 12, wherein the non-transitory computer-readable medium is a random access memory (RAM), a read-only memory (ROM), a flash memory, or a hard disk.

* * * * *